United States Patent
Schewe et al.

(10) Patent No.: US 7,985,063 B2
(45) Date of Patent: Jul. 26, 2011

(54) MOLDS AND RELATED METHODS AND ARTICLES

(75) Inventors: Scott R. Schewe, Eden Prairie, MN (US); Jeffrey S. Lindquist, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1027 days.

(21) Appl. No.: 11/832,878

(22) Filed: Aug. 2, 2007

(65) Prior Publication Data

US 2007/0267780 A1    Nov. 22, 2007

Related U.S. Application Data

(62) Division of application No. 10/742,278, filed on Dec. 19, 2003, now abandoned.

(51) Int. Cl.
    B29C 33/38    (2006.01)
(52) U.S. Cl. ............... 425/403; 249/112; 249/114.1; 249/117; 425/470
(58) Field of Classification Search .......... 425/403, 425/470, 522; 249/112, 114.1, 115, 117, 249/160

See application file for complete search history.

(56) References Cited

U.S. PATENT DOCUMENTS

| | | | |
|---|---|---|---|
| 4,002,709 A | 1/1977 | Mozer | |
| 4,482,518 A | 11/1984 | Brady, Jr. | |
| 4,490,421 A * | 12/1984 | Levy | 264/573 |
| 4,501,545 A | 2/1985 | Divoky | |
| 4,913,642 A | 4/1990 | Weber | |
| 4,952,357 A | 8/1990 | Euteneuer | |
| 4,963,313 A | 10/1990 | Noddin et al. | |
| 5,087,394 A | 2/1992 | Keith | |
| 5,195,969 A | 3/1993 | Wang et al. | |
| 5,254,091 A * | 10/1993 | Aliahmad et al. | 604/103.06 |
| 5,304,340 A | 4/1994 | Downey | |
| 5,334,146 A | 8/1994 | Ozasa | |
| 5,449,371 A | 9/1995 | Pinchuk et al. | |
| 5,500,181 A | 3/1996 | Wang et al. | |
| 5,522,961 A | 6/1996 | Leonhardt | |
| 5,525,388 A | 6/1996 | Wand et al. | |
| 5,714,110 A | 2/1998 | Wang et al. | |
| 5,733,301 A | 3/1998 | Forman | |
| 5,759,474 A | 6/1998 | Rupp et al. | |
| 5,807,520 A | 9/1998 | Wang et al. | |
| 5,948,345 A | 9/1999 | Patel et al. | |
| 5,951,941 A | 9/1999 | Wang et al. | |
| 6,024,752 A | 2/2000 | Horn et al. | |
| 6,143,230 A | 11/2000 | Andrios et al. | |

(Continued)

FOREIGN PATENT DOCUMENTS

EP    1344547    9/2003

(Continued)

OTHER PUBLICATIONS

U.S. Appl. No. 09/950,195, filed Sep. 10, 2001.

(Continued)

*Primary Examiner* — James Mackey
(74) *Attorney, Agent, or Firm* — Seager, Tufte & Wickhem, LLC

(57) ABSTRACT

Molds and related methods and articles are disclosed. In certain embodiments, an exposed surface of the mold has regions with different coefficients of friction.

16 Claims, 7 Drawing Sheets

U.S. PATENT DOCUMENTS

| | | |
|---|---|---|
| 6,168,748 B1 | 1/2001 | Wang et al. |
| 6,176,698 B1 | 1/2001 | Grantz et al. |
| 6,221,042 B1 | 4/2001 | Adams |
| 6,328,710 B1 | 12/2001 | Wang et al. |
| 6,458,313 B2 | 10/2002 | Hudgins et al. |
| 6,527,741 B1 | 3/2003 | Lee et al. |
| 6,561,788 B1 | 5/2003 | Gaudoin |
| 6,645,422 B2 | 11/2003 | Jung, Jr. et al. |
| 6,652,485 B1 | 11/2003 | Gaudoin et al. |
| 6,784,397 B2 * | 8/2004 | Li et al. .......................... 425/89 |
| 6,835,059 B2 * | 12/2004 | Skinner et al. ................ 425/182 |
| 6,875,197 B1 * | 4/2005 | Simhambhatla et al. .. 604/96.01 |
| 6,881,209 B2 * | 4/2005 | Boatman et al. .............. 264/512 |
| 6,946,092 B1 * | 9/2005 | Bertolino et al. ............. 264/512 |
| 6,955,658 B2 * | 10/2005 | Murray, III ................... 425/470 |

| | | |
|---|---|---|
| 2002/0041058 A1 | 4/2002 | Murphy |
| 2002/0110657 A1 | 8/2002 | Wang et al. |
| 2003/0004535 A1 | 1/2003 | Musbach et al. |

FOREIGN PATENT DOCUMENTS

| | | |
|---|---|---|
| JP | 07276484 | 10/1995 |
| WO | WO 02098498 | 6/2002 |

OTHER PUBLICATIONS

"Blasformen en Miniature." Plastverarbeiter, Zechner und Huethig Verlag GMBH. Speyer/Rhein, DE, vol. 47, No. 11, Nov. 1996, pp. 70-72.

Certified translation of "Blasformen en Miniature." Plastverarbeiter, Zechner und Huethig Verlag GMBH. Speyer/Rhein, DE, vol. 47, No. 11, Nov. 1996, pp. 70-72.

* cited by examiner

MOLDS AND RELATED METHODS AND ARTICLES

RELATED APPLICATIONS

This application is a divisional of and claims priority under 35 U.S.C. §120 to U.S. patent application Ser. No. 10/742,278, filed on Dec. 19, 2003, the entire contents of which are hereby incorporated by reference.

TECHNICAL FIELD

This invention relates to molds and related methods and articles.

BACKGROUND

Medical balloons are used in a variety of applications including, for example, angioplasty and stent delivery. In general, a medical balloon has a body region, a waist region and a cone region joining the body and waist region.

SUMMARY

In one aspect, the invention features a mold having an exposed surface defining a mold cavity that has a body region, a waist region and a cone region connecting the body and wait regions. A first portion of the exposed surface of the cavity has a first coefficient of friction, and a second portion of the exposed surface has a second coefficient. The first coefficient of friction is different from the second coefficient of friction.

In another aspect, the invention features a mold having an exposed surface defining a cavity within the mold. The mold includes a mold body that has a body region, a waist region and a cone region connecting the body and waist regions. The mold also includes at least one insert is supported by the mold body so that at least one insert forms at least a portion of the exposed surface of the mold.

In a further aspect, the invention features a mold having an exposed surface defining a cavity within the mold. The mold includes a mold body having a body region, a waist region and a cone region connecting the body and waist regions. The mold also includes a coating that is supported by the mold body so that the coating forms at least a portion of the exposed surface of the mold.

In an additional aspect, the invention features a mold having an exposed surface defining a mold cavity. The mold cavity has a body region, a waist region and a cone region connecting the body and waist regions. The mold is formed of a composite including a mold material and a mold additive material.

In one aspect, the invention features a medical device that includes a shaft. The shaft includes a lumen and a balloon in fluid communication with the lumen of the shaft. The balloon has a body region, a waist region and a cone region connecting the body and waist regions. The body region of the balloon has an expanded diameter that is at least 3.5 times an outer diameter of the shaft, and a thickness of the balloon in the cone region varies by less than about 50 percent.

In another aspect, the invention features a medical device that includes a shaft. The shaft includes a lumen and a balloon in fluid communication with the lumen of the shaft. The balloon has a body region, a waist region and a cone region connecting the body and waist regions. The body region of the balloon has an expanded outer diameter that is at least about 3.5 times an outer diameter of the shaft, and the cone region of the balloon has a compressed profile diameter of less than about four times an outer diameter of the shaft, with the balloon in a wound position.

Embodiments can include one or more of the following features.

In some embodiments, the first coefficient of friction can be at most about 0.8 (e.g., at most about 0.4).

In certain embodiments, the ratio of the first coefficient of friction to the second coefficient of friction is less than about 0.5.

In some embodiments, the first portion of the exposed surface is contained within only one region selected from the body region, the waist region and the cone region (e.g., within only the waist region).

In certain embodiments, the first portion is contained within only two regions selected from the body region, the waist region and the cone region. (e.g., within only the waist and cone regions).

In some embodiments, the first portion is contained within the waist, cone and body regions.

In certain embodiments, the mold includes a mold body and a coating supported by the mold body so that the coating forms the first portion of the exposed surface of the mold. The mold can be, for example, an anodized coating (e.g., a hard-coat anodized coating).

In some embodiments, the coating is a vapor deposited coating or a liquid deposited coating. The coating can be formed of, for example, fluorinated polymers, carbon-based materials, silicones, polyethylenes, modified tungsten disulfide and/or polyetheretherketones.

In certain embodiments, the mold includes a mold body and an insert supported by the mold body so that the insert forms the first portion of the exposed surface of the mold. The insert can be, for example, removably positioned within the mold body. The insert can be one piece, or more than one piece. For example, the mold body can include first and second pieces configured to fit together to form the mold cavity, and the insert can include first and second pieces, where the first piece of the insert is supported by the first piece of the mold body, and the second piece of the insert is supported by the second piece of the mold body. The insert can be formed of, for example, fluorinated polymers, carbon-based materials, silicones, polyethylenes, modified tungsten disulfide, and/or polyetheretherketones. The mold body can include at least two axially adjacent pieces configured to fit together to form the mold cavity.

In some embodiments, the first portion of the exposed surface can be a composite material including a mold material and a mold material additive. The mold material can have a higher coefficient of friction than the mold material additive. The mold material additive can be homogeneously incorporated in the mold material. Examples of mold materials include stainless steel, stainless steel alloys, aluminum, aluminum alloys, glass, quartz and/or copper alloys. Examples of mold material additives include fluorinated polymers, carbon-based materials, silicones, polyethylenes, modified tungsten disulfide, and/or polyetheretherketones.

In certain embodiments, the first portion of the exposed surface can be formed of, for example, fluorinated polymers, fluorinated polymers, carbon-based materials, silicones, polyethylenes, modified tungsten disulfide, and/or polyetheretherketones.

In some embodiments, the waist region of the mold cavity has an inner diameter of greater than about 0.75 mm. In certain embodiments, the body region of the mold cavity has an inner diameter of at most about 40 mm. In some embodiments, the cone region of the mold cavity has a taper of at least about 10 degrees. In certain embodiments, the mold cavity has a maximum inner diameter of at most about 40 mm and the mold cavity has a minimum inner diameter within the cavity of at most about 1 mm.

In certain embodiments, the mold includes a mold body with first and second pieces, where the first and second pieces are configured to releasably fit together to define the mold cavity. The first portion can be axially adjacent the second portion, and the first portion can form the body region and the second portion forming the cone region. The mold body can include a third piece that forms a second cone region.

In some embodiments, first and second inserts are used, with the first and second inserts being supported by an exposed surface of the mold. At least one of the inserts can disposed on an exposed surface of the mold.

In certain embodiments, the mold also includes a tie material between the an insert and an exposed surface of the mold. The tie material can be, for example, an adhesive. The tie material can permanently bond one or more inserts to the exposed surface.

In some embodiments, an insert has a coefficient of friction that is less than the coefficient of friction of an exposed surface of the mold.

In certain embodiments, the expanded outer diameter of the body region of the balloon is at least about four times (e.g., at least about 4.5 times) the outer diameter of the shaft.

In some embodiments, the thickness of the balloon in the cone region of the balloon varies by less than about 40 percent.

In certain embodiments, the balloon is a coronary balloon, an aortic balloon, a peripheral balloon, a reperfusion balloon, an endoscopy balloon, a urology balloon and/or a neurology balloon.

In some embodiments, the balloon has a compressed profile diameter of less than about 4 mm in a wound position.

In certain embodiments, the cone region of the balloon has a wall thickness of less than about 0.005 inch.

In some embodiments, the shaft and the balloon are contiguous.

Embodiments can have one or more of the following advantages.

In some embodiments, a molding material (e.g., material used to form a medical device, such as a medical balloon) placed within the mold can contact portions of the exposed surface having a coefficient of friction less than a coefficient of friction of surfaces formed by the mold material during formation (e.g., radial and/or axial expansion/contraction). Contact between relatively low-friction portions of the mold and the molding material can reduce stresses during molding processes.

In certain embodiments, a medical device (e.g., a medical balloon) can be provided having a more consistent wall thickness within regions of the medical device including, for example, within the cone regions of the balloon. Balloons can be produced relatively consistently and relatively predictably. In some cases, medical balloons can be formed having relatively large expanded diameters within the body region of the balloon and relatively small compressed diameters when wrapped about the shaft of a catheter. This can facilitate delivery of balloons having relatively large diameters, as expanded, through relatively narrow lumens of a patient's body.

DESCRIPTION OF DRAWINGS

Like reference symbols in the various drawings indicate like elements.

DETAILED DESCRIPTION

Figure 1:
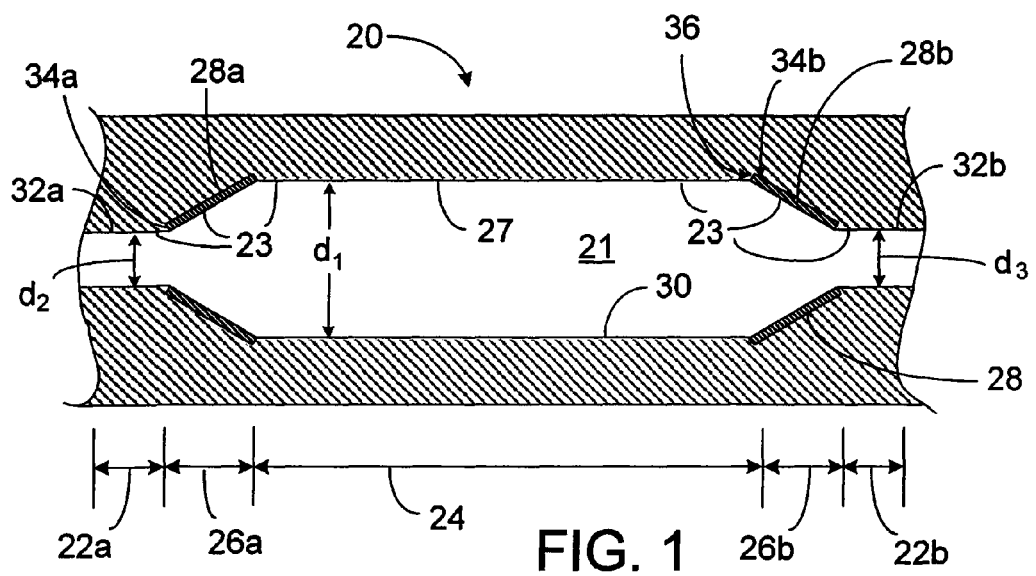
FIG. 1 is a cross-sectional view of an embodiment of a mold.

FIG. 1 shows a mold 20, which can be used to form a medical balloon (e.g., a coronary balloon, an aortic balloon, a peripheral balloon, a reperfusion balloon, an endoscopy balloon, a urology balloon, a neurology balloon). Mold 20 includes an exposed surface 23 that forms a mold cavity 21 having a suitable shape for forming the medical balloon. Cavity 21 has waist regions 22a and 22b, a body region 24 and cone regions 26a and 26b positioned between the waist and body regions. Each region of mold 20 corresponds to a region of a molded medical balloon, which will be described in further detail below.

Mold 20 is designed so that exposed surface 23 has portions of differing coefficients of friction. Cavity 21 includes portions 28a and 28b (located within cone regions 26a and 26b, respectively) having a coefficient of friction that is different from the coefficient of friction of portion 30 (located within body region 24) and the coefficient of friction of portions 32a and 32b (located within waist regions 22a and 22b, respectively).

In certain embodiments, the coefficient of friction of portions 28a and 28b is at most about 0.8 (e.g., at most about 0.7, at most about 0.6, at most about 0.5, at most about 0.4, at most about 0.3, at most about 0.2, at most about 0.1, from 0.02 to about 0.1, from about 0.02 to about 0.3). As referred to herein, the coefficient of friction of a material is measured according to ASTM D1894-01.

In certain embodiments, the ratio of the coefficient of friction of portions 28a and 28b to the coefficient of friction of portion 30 and/or portions 32a and 32b is at most about 0.5 (e.g., at most about 0.4, at most about 0.3, at most about 0.2, at most about 0.1).

Examples of materials from which portions 28a and 28b can be formed include fluorinated polymers, such as Teflon® fluorinated polymers, carbon-based materials, silicones, polyethylenes, modified tungsten disulfide and polyetheretherketones. Examples of fluorinated polymers include polytetrafluoroethylenes, polyvinylidinefluorides, fluorinated ethylene propylenes, perfluoroalkoxy polymers, tetrafluoroethylene perfluoromethylvinylethers, thylene tetrafluoroethylene, and polytetrafluoroethylene-perfluoromethylvinylether copolymers.

Examples of materials from which portion 30 and/or portions 32a and 32b of mold cavity 21 can be formed include standard mold materials, such as stainless steel, aluminum, aluminum alloys, such as 6061 aluminum, glass, quartz, copper alloys and steel alloys.

As an example, in some embodiments, portions 30, 32a and 32b are formed of a material having a coefficient of friction of about 0.45 (e.g., aluminum) and portions 28a and 28b are formed of a material having a coefficient of friction of less than 0.45 (e.g., polytetrafluoroethylene). As another example, in certain embodiments, portions 30, 32a and 32b are formed of a material having a coefficient of friction of about 0.8 (e.g., stainless steel) and portions 28a and 28b are formed of a material having a coefficient of friction of less than 0.8 (e.g., polytetrafluoroethylene).

In some embodiments, portions 28a and 28b define a coating disposed in recessed regions 34a and 34b, respectively, of the body of mold 20. In some embodiments, the coating is an anodized coating (e.g., a hardcoat anodized coating). Such a coating can be formed, for example, by oxidizing the region of the mold body corresponding to portions 28a and 28b.

In some embodiments, the method (e.g., anodic reaction given by $2Al+3H_2O=6e^-+Al_2O_3+6H^+$ and cathodic reaction given by $2H^++2e^-=H_2$) includes forming portions 28a and 28b from aluminum to form an anode. After forming the anode, portions 28a and 28b of the mold body can be pretreated to remove grease and oxide from the surface by placing portions 28a and 28b in a cleaning solution. For example, in some cases, portions 28a and 28b are submerged in a solution containing 1M NaOH for about one minute and then in a solution containing 0.2M $HNO_3$ for about two seconds. Subsequent to pretreating portions 28a and 28b, the portions are placed in an anodizing solution along with a cathode. An example of a suitable anodizing solution contains 2.2M $H_2SO_4$+50 g/l $H_2C_2O_4$. The amount of anodizing solution used can vary depending, for example, on the size of the mold. During the forming process, the anodizing solution is maintained at a suitable temperature (e.g., about 25° C.) or range of temperatures. After forming the oxide layer, the oxidized surface can provide a suitable paint base. In some embodiments, a 13 g/l sanodal dye at pH=5.75 is applied (e.g., by dipping) to the anodized surface at a temperature of 65° C. Portions 28a and 28b can then be immersed in boiling water to seal any pores in the aluminum oxide.

In certain embodiments, the coating can be formed by a deposition process. Examples of deposition processes include vapor deposition processes (e.g., chemical vapor deposition processes, physical vapor deposition processes) and liquid deposition processes (e.g., solution deposition processes, sol gel deposition processes).

Figure 2A:
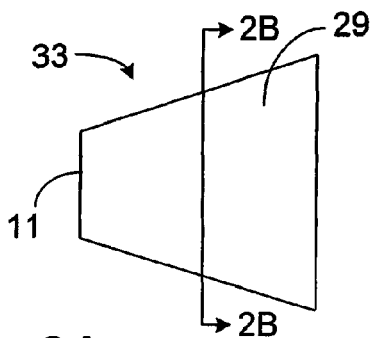
FIG. 2A and 2B are side and end views, respectively, of an embodiment of an insert.
Figure 2B:
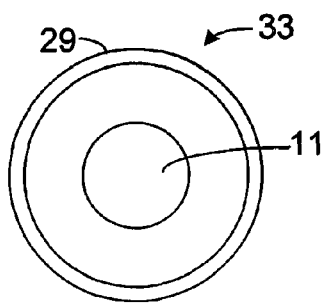
Figure 3A:
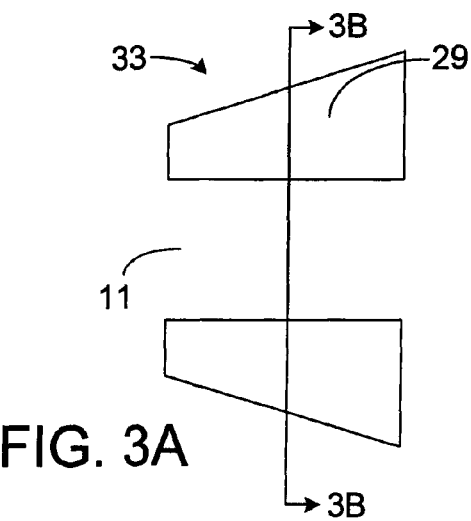
FIGS. 3A and 3B are side and end views, respectively, of an embodiment of a clamshell-type insert.
Figure 3B:
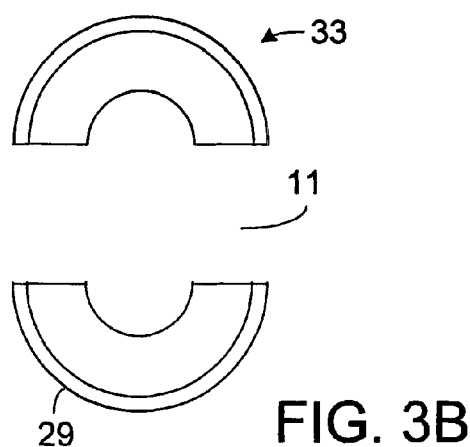

In certain embodiments, portions 28a and 28b are inserts (e.g., pre-molded inserts) that are supported by the mold body within recessed regions 34a and 34b, respectively, of the body of mold 20. The inserts can be removable from the mold body, or the inserts can be non-removable from the mold body (e.g., bonded to the mold body by a tie layer, such as an adhesive layer). An insert can be formed of one piece or multiple pieces. As an example, FIGS. 2A and 2B show an insert 33 having an outer surface 29 and an inner opening 11 where the insert is formed of a single piece. As another example, FIGS. 3A and 3B show an insert 33 having an outer surface 29 and an inner opening 11 where the insert is formed of two pieces (in a clam shell configuration).

In some embodiments, portions 28a and 28b are formed of a composite material disposed within recessed regions 34a and 34b, respectively, of the body of mold 20. A composite material can contain, for example, one or more standard mold materials (e.g., stainless steel, aluminum, aluminum alloys, glass, quartz, copper alloys, and/or steel alloys) and one or relatively low coefficient of friction materials (e.g., polytetrafluoroethylene, polyvinylidinefluoride, fluorinated ethylene propylene, perfluoroalkoxy, tetrafluoroethylene perfluoromethylvinylether, thylene tetrafluoroethylene and/or polytetrafluoroethylene-perfluoromethylvinylether copolymer). The materials in the composite material can be homogeneously mixed or nonhomogeneously mixed. The relatively low coefficient of friction material (mold additive) can be added to the mold material by processes such as impregnation and/or infiltration, and/or the mold additive can be in powder form and mixed with other mold material powders prior to formation of the mold 20 using any suitable powder metallurgy technique (e.g., die compacting) or alloying technique.

In general, the diameter $d_1$ of cavity 21 is selected based upon the intended use of the article (e.g., medical device) that is to be molded using mold 20. For example, in embodiments in which mold 20 is used to prepare a medical balloon, $d_1$ can be at most about 40 millimeters (mm) (e.g., at most about 35 mm, at most about 30 mm, at most about 25 mm, at most about 20 mm, at most about 16 mm, at most about 8 mm, at most about five mm, at most about two mm, at most about one mm).

Typically, the diameter $d_2$ of cavity 21 is smaller than the diameter $d_1$ of cavity 21. Generally, the diameter $d_2$ of cavity 21 is also selected based upon the intended use of the article (e.g., medical device) that is to be molded using mold 20. For example, in embodiments in which mold 20 is used to prepare a medical balloon, $d_2$ can be greater than about 0.75 mm (e.g., greater than about one mm, greater than about two mm, greater than about three mm, greater than about five mm). In some embodiments, $d_2$ can be at most about five mm (e.g., at most about four mm, at most about three mm, at most about two mm, at most about one mm).

Typically, the diameter $d_3$ of cavity 21 is about the same as or smaller than diameters $d_1$ and $d_2$ of cavity 21. Generally, the diameter $d_3$ of cavity 21 is also selected based upon the intended use of the article (e.g., medical device) that is to be molded using mold 20. For example, in embodiments in which mold 20 is used to prepare a medical balloon, $d_3$ can be greater than 0.75 mm (e.g., greater than about one mm, greater than about two mm, greater than about three mm, greater than about five mm). In some embodiments, $d_3$ can be at most about five mm (e.g., at most about four mm, at most about three mm, at most about two mm, at most about one mm).

In general, cone regions 26a and 26b are tapered from diameter $d_1$ to diameters $d_2$ and $d_3$, respectively. In certain embodiments, the taper of cone regions 26a and/or 26b is at least about 10° (e.g., at least about 15°, at least about 20°, at least about 30°, at least about 40°, at least about 50°), such as about 25°. In some embodiments, the taper of cones 26a and/or 26b is at most about 85° (e.g., at most about 80°, at most about 75°, at most about 70°).

Figure 4:
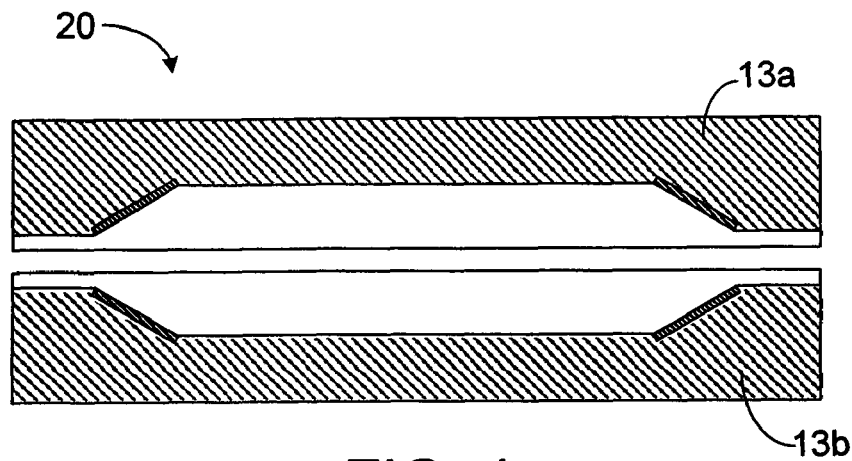
FIG. 4 is a cross-sectional view of an embodiment of a clamshell-type mold.
Figure 5:
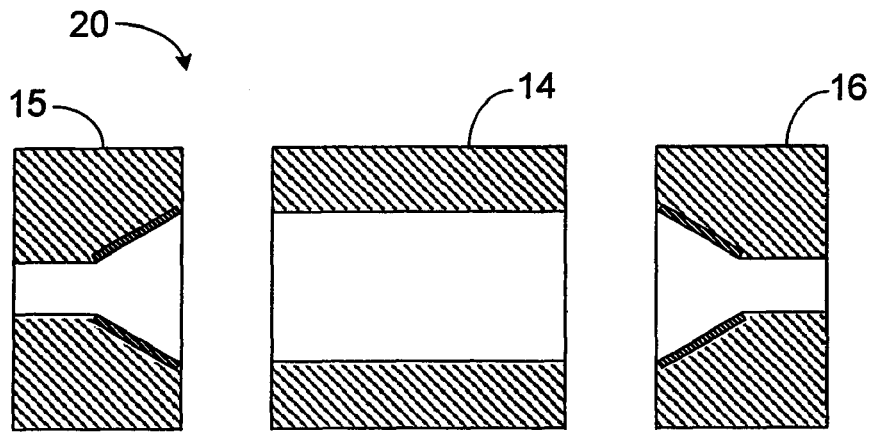
FIG. 5 is a cross-sectional view of an embodiment of a sectional mold.

Mold 20 can be a single-piece mold, or mold 20 can be formed of multiple pieces. As an example, as shown in FIG. 4, mold 20 can be formed of pieces 13a and 13b that fit together in a clam shell configuration. As another example, FIG. 5 shows a mold 20 formed of axially adjacent pieces 14, 15 and 16 that fit together. As shown in FIG. 5, piece 14 corresponds to body region 24. In general, however, the pieces of a multipiece mold can correspond to any desired region or regions of mold 20. As an example, in certain embodiments, one piece of the mold can correspond to body region 24 and two other pieces of the mold can correspond to cone regions 26a and 26b, respectively. In embodiments in which mold 20 is formed of multiple pieces, the pieces can be designed to releasably fit together, or to fit together in a non-releasable fashion.

Figure 6A:
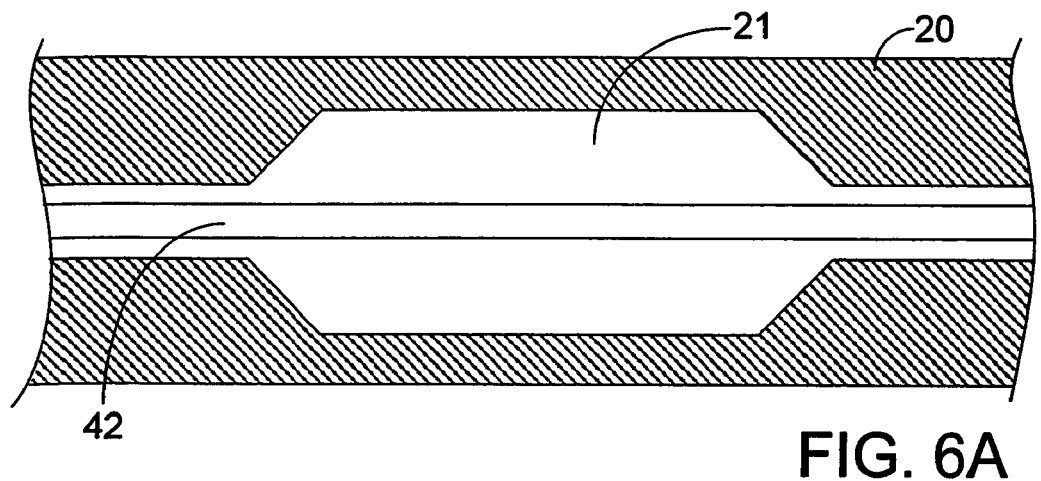
FIGS. 6A-6C illustrate an embodiment of a method of forming a balloon.
Figure 6B:
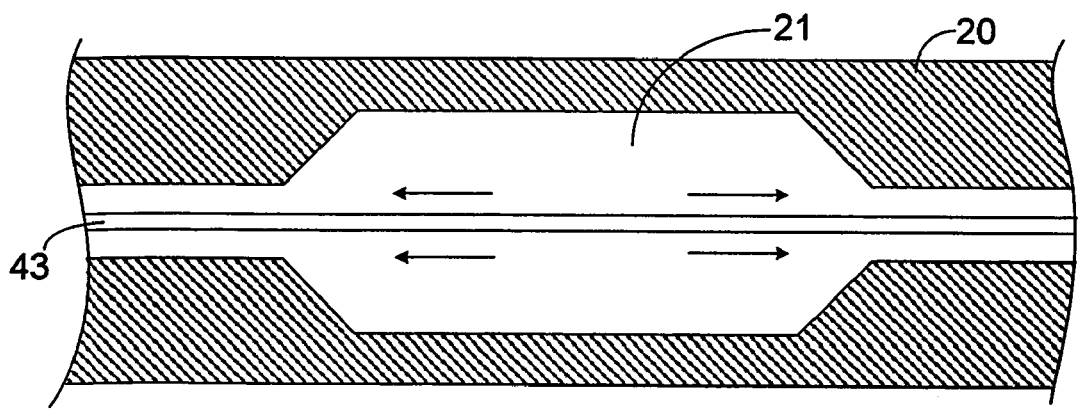
Figure 6C:
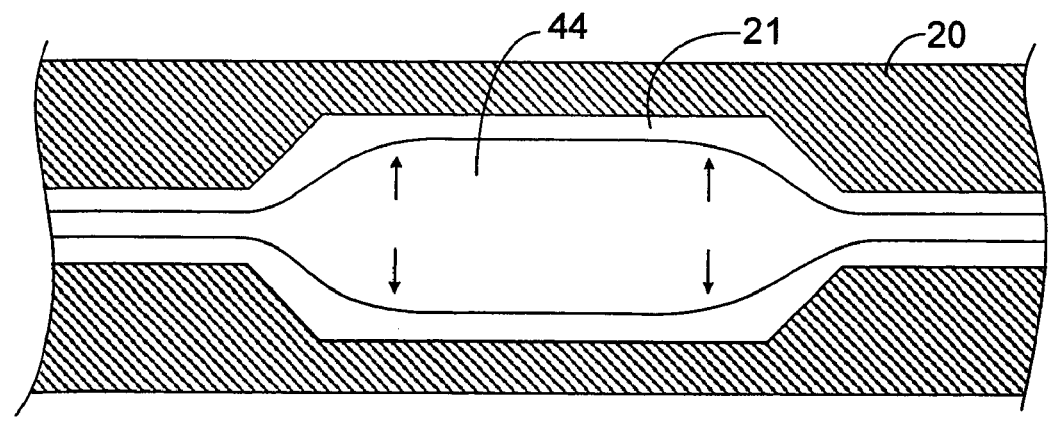

FIG. 6A-6C illustrate a typical embodiment of a method of forming a medical balloon using mold 20. As shown in FIG. 6A, an elongated tube of material 42 (e.g., a parison) is disposed within cavity 21. Referring to FIG. 6B, tube 42 is axially stretched (as indicated by the arrows) and heated (e.g., by heating mold 20) to form a stretched tube 43. As shown in FIG. 6C, tube 43 is heated while pressurizing the interior of tube 43 (without exerting an axial stress on tube 42) to deform tube 43 and form a balloon 44.

Typically, tube 42 is heated to a temperature sufficient to soften the material from which tube 42 is formed so that the tube can be stretched. For example, tube 42 can be heated to its glass transition temperature, or higher. In some embodiments, tube 42 is heated to a temperature of from about 50° C. to about 125° C., such as about 100° C.

In general, the axial stress exerted on tube 42 during axial stretching is at least about 50 g (e.g., at least about 1,000 g, at least about 10,000 g) and/or at most about 30,000 g (e.g., at most about 20,000 g).

Generally, during the formation of balloon 44, tube 43 is heated to a temperature sufficient to soften the material from which tube 43 is formed so that the tube can be deformed to form a balloon. For example, tube 42 can be heated to its glass transition temperature, or higher. In some embodiments, tube 43 is heated from about 70° C. to about 125° C., such as about 100° C.

Typically, the internal pressure of tube 43 during the formation of balloon 44 is at least about 200 psi (e.g., at least about 500 psi) and/or at most about 1,000 psi (e.g., at most about 750 psi), such as 350 psi.

Examples of methods of forming a medical balloon using a mold are disclosed, for example, in U.S. Pat. No. 5,714,110 and U.S. patent application Ser. No. 09/950,195, entitled "Medical Balloon," both of which are hereby incorporated by reference.

Figure 7:
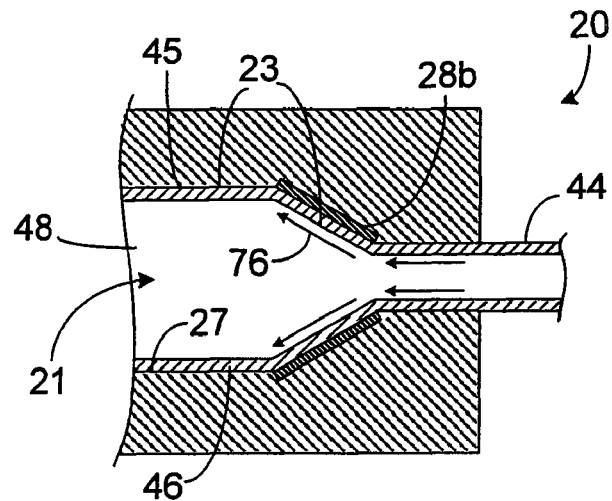
FIG. 7 is a cross-sectional view along line 7 of FIG. 6C of a balloon being formed within a mold.

FIG. 7 illustrates a portion of the balloon molding process in which a stretched tube is being deformed to form a balloon. During this process, an outer surface 45 of a deforming tube 48 contacts exposed surface 23 of mold cavity 21. Due to radial expansion of deforming tube 48, the material from which deforming tube 48 is made flows toward the center of a body region 46 of the deforming tube, generally in the direction of arrows 76. As the tube material flows, outer surface 45 of deforming tube 48 slides along exposed surface 23 of mold 20.

Without wishing to be bound by theory, it is believed that variations in wall thickness in the balloon, particularly within the cone regions of the balloon, can be the result of frictional sliding between the outer surface of the deforming tube and the exposed surface of the cavity, which occurs during radial expansion. It is believed that variations in wall thickness of the balloon cone regions can increase the profile of the balloon when wrapped about a shaft, which, in turn, affects its deliverability and determines the lumen size through which the balloon can be delivered. It is further believed that variations in the wall thickness of the balloon cone regions can result in a balloon that has relatively limited useful lifetime (e.g., does not show the ability to reproducibly expand and contract in a sufficiently predictable manner). In particular, it is believed that failure points are frequently located near regions of inconsistent wall thickness, and that variation in wall thickness can also affect the fatigue resistance of the balloon. These failure points due to inconsistent wall thickness can also limit the expansion size and/or ultimate burst strength of the balloon for a given catheter shaft size.

By forming portions 28a and 28b from a relatively low coefficient of friction material, it is believed that stresses resulting from frictional sliding between outer surface 45 of deforming tube 48 and the exposed surface 23 of mold 20 can be reduced. It is believed that this reduction in frictional sliding can result in more consistent wall thickness within various regions of the balloon and from balloon to balloon, and can also allow for formation of a balloon having desirable dimensional qualities (e.g., relatively small variation in wall thickness in the cone regions, relatively high ratio of expanded outer diameter to shaft diameter, relatively small compressed, relatively small wrapped delivery profile, relatively small wall thickness).

Figure 8:
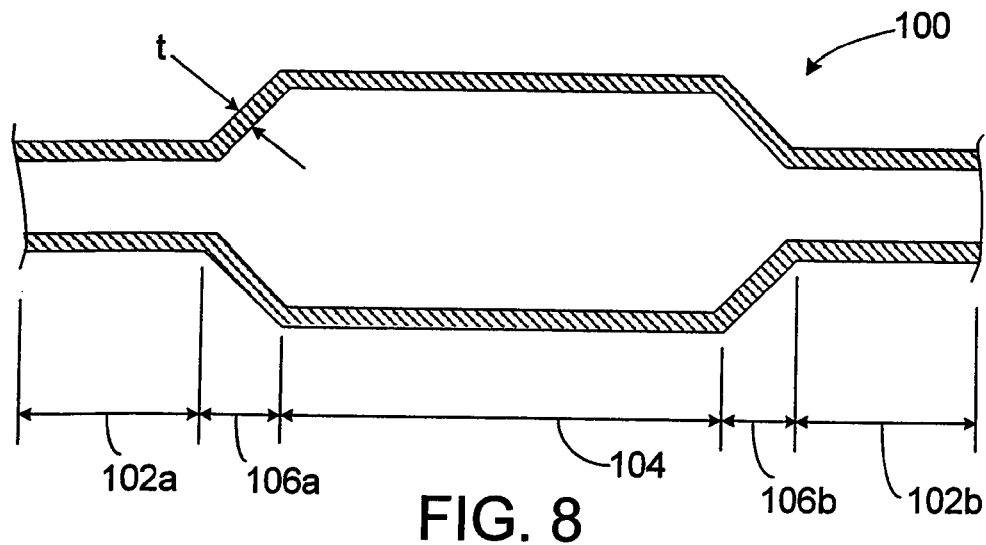
FIG. 8 is a cross-sectional view of an embodiment of a balloon.

Referring now to FIG. 8, a medical balloon 100 has a body region 104, waist regions 102a and 102b, and cone regions 106a and 106b located between the body and waist regions.

The wall thickness t within cone regions 106a and 106b can be relatively small. In some embodiments, the wall thickness t of cone regions 106a and 106b is less than about 0.005 inch (e.g., less than about 0.003 inch, less than about 0.001 inch, from about 0.001 inch to about 0.005 inch).

The variation in the wall thickness t of balloon 100 in cone regions 106a and 106b can be relatively small. In certain embodiments, the variation in the wall thickness t of balloon 100 in regions 106a and 106b is less than about 50 percent (e.g., less than about 40 percent, less than about 30 percent, less than about 20 percent, less than about 10 percent).

Figure 9:
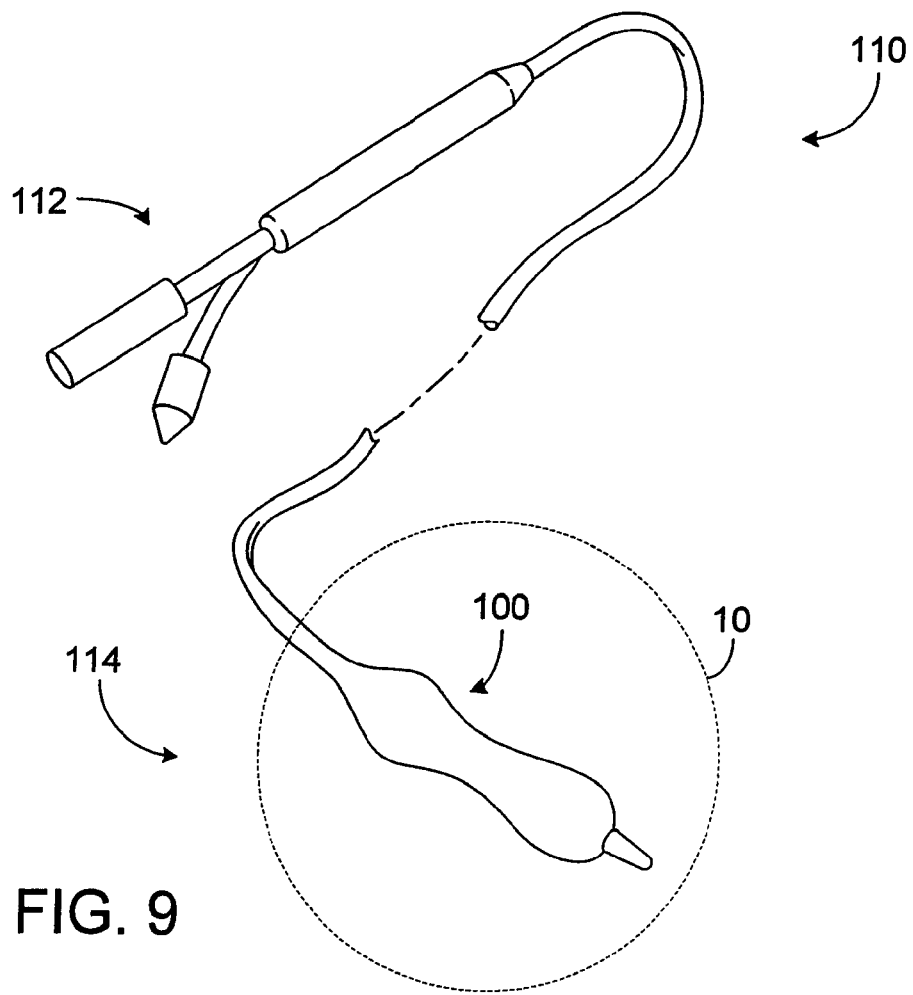
FIG. 9 is an elevational view of a balloon catheter.

FIG. 9 shows a balloon catheter 110 that includes a proximal end 112 and a distal end 114. Located near distal end 114 is balloon 100 that is contiguously attached to catheter 110 and configured to inflate and deflate within a lumen of a patient's body. In some embodiments, balloon 100 is positioned on a shaft of catheter 110, and wrapped about catheter 110 to form a compressed profile. In some cases, a stent is positioned about wrapped balloon 100 and delivered to a desired location within the patient's body. Balloon 100 is then expanded to force the stent to expand within the lumen. Balloon 100 can then be deflated and removed from the lumen of the patient. In certain embodiments, balloon 100 is expanded without a stent being present (e.g., balloon 100 is expanded to dilate a lumen).

Figure 10:
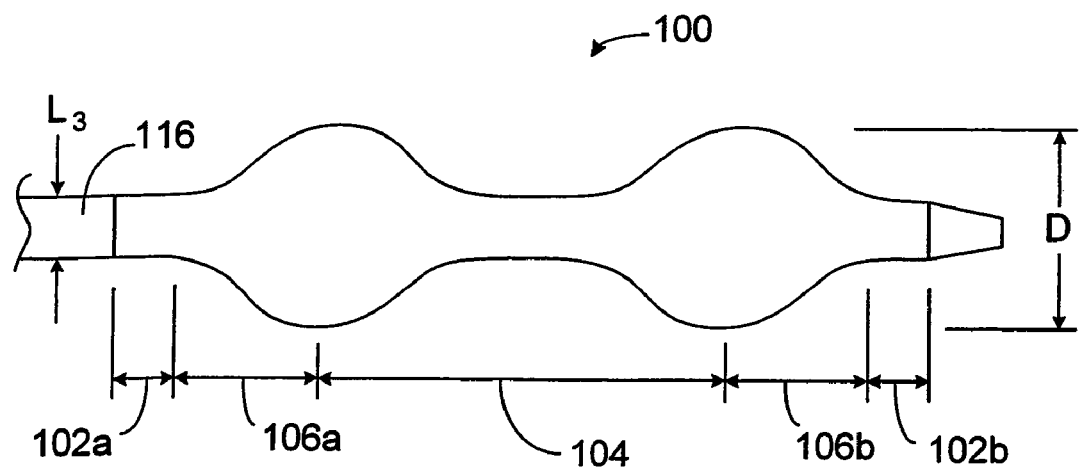
FIG. 10 is a detailed side view of a balloon in a wrapped condition along line 10 of FIG. 9.

FIG. 10 illustrates balloon 100 in a compressed profile condition. As above, balloon 100 includes waist regions 102a and 102b, body region 104 and cone regions 106a and 106b. In some cases, balloon 100 is attached to catheter shaft 116 and is in communication with an inflation port that serves to inflate balloon 100 when balloon 100 is in a desired position within the lumen of a patient. Balloon 100 can also be utilized for lumen dilation, e.g., without the stent.

Generally, when in a wound position, balloon 100 has its maximum compressed profile diameter D in cone regions 106a and 106b. In some embodiments, the maximum compressed diameter D of balloon 100 when in a compressed condition is less than about four mm (e.g., less than about two mm, less than about one mm, from about one mm to about four mm). In certain embodiments, the maximum compressed diameter D of balloon 100 when in a compressed condition is less than about four (e.g., less than about three, less than about 1.5) times the outer diameter $L_3$ of shaft 116.

Figure 11:
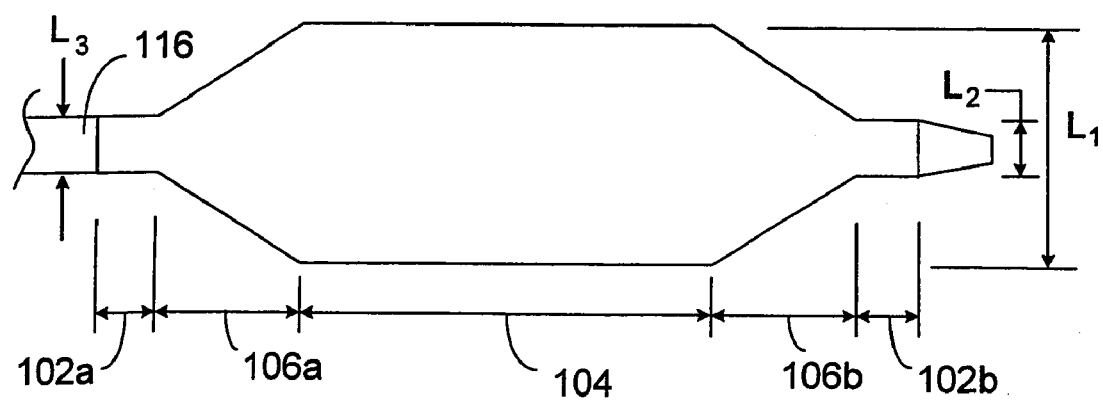
FIG. 11 is a side view of a balloon in an expanded condition.

FIG. 11 illustrates balloon 100 in an expanded state with a maximum outer expanded diameter $L_1$ located within a body region 104. The value of $L_1$ generally depends upon the intended use of balloon 100. In some embodiments, $L_1$ is at most about 40 mm (e.g., at most about 35 mm, at most about 30 mm, at most about 25 mm, at most about 20 mm, at most about 15 mm, at most about 10 mm).

In its expanded state, balloon 100 has a minimum expanded diameter $L_2$ within waist region 102. In some embodiments, $L_1$ is at least about 3.5 (e.g., at least about four, at least about 4.5, at least about five) times $L_3$.

Balloon 100 can be formed of a resilient material, such as a polymer, that is capable of being inflated and deflated in a patient. In some cases, the balloon material is relatively stable upon crystallization. Examples of polymers include polyamides (e.g., nylons), copolymers of polyamides (e.g., nylon-polyether copolymers), polyesters (e.g., polyethylene terephthalate (PET) polymers, polybutylene terephthalate (PBT) polymers), copolymers of polyesters, polyetheretherketones (PEEKs), polyethylenenaphthalates (PEN polymers), polyurethanes, polyethylenes, polypropylenes, copolymers and ionomers of ethylene, copolymers and ionomers of polypropylene, polystyrenes and copolymers of polystyrenes. Examples of commercially available polyesters include the Selar PT family of polymers (e.g., Selar PT 8307, Selar PT4274, Selar PTX280), which are commercially available from E. I. DuPont de Nemours (Wilmington, Del.), the Cleartuf family of polymers (e.g., Cleartuf 8006), which are commercially available from M&G Polymers (Apple Grove, W. Va.), the Traytuf family of polymers (e.g., Traytuf 1006), which are commercially available from the Shell Chemical (Houston, Tex.), the Melinar family of polymers, commercially available from E. I. DuPont de Nemours (Wilmington, Del.), the Celanex family of polymers, commercially available from Ticona (Summit, N.J.), the Riteflex family of polymers, commercially available from Ticona (Summit, N.J.), the Hytrel family of polymers (e.g., Hytrel 5556, Hytrel 7246, Hytrel 4056), commercially available from E. I. DuPont de Nemours (Wilmington, Del.), the Arnitel family of polymers (e.g., Arnitel EM630), commercially available from DSM (Erionspilla, Ind.). Examples of commercially available polyamides include Nylon 12, commercially available from Atofina (Philadelphia, Pa.), Nylon 6, commercially available from Honeywell (Morristown, N.J.), Nylon 6/10, commercially available from BASF (Mount Olive, N.J.), Nylon 6/12, commercially available from Ashley Polymers (Cranford, N.J.), Nylon 11, Nylon MXD-6, and the Grivory family of polymers, commercially available from EMS (Sumter, S.C.), the Grilamid family of polymers (e.g., Grilamid L25, Grilamid L20), commercially available from EMS (Sumter, S.C.), the Vestamid family of polymers (e.g., Vestamid L2101F), commercially available from Daicel-Degussa Ltd., and the PEBAX family of polymers (e.g., PEBAX 5533, PEBAX 2533, PEBAX 7033), commercially available from Atofina (Philadelphia, Pa.), the Trogamid family of polyamides from Daicel-Degussa, Crystamid MS 1100 from Atofina (Philadelphia, Pa.), and Vestamid L2101 F nylon 12 from Degussa AG. An example of a commercially available polyethylene is Marlex 4903 high density polyethylene from Phillips 66 (Bartlesville, Okla.).

Figure 12:
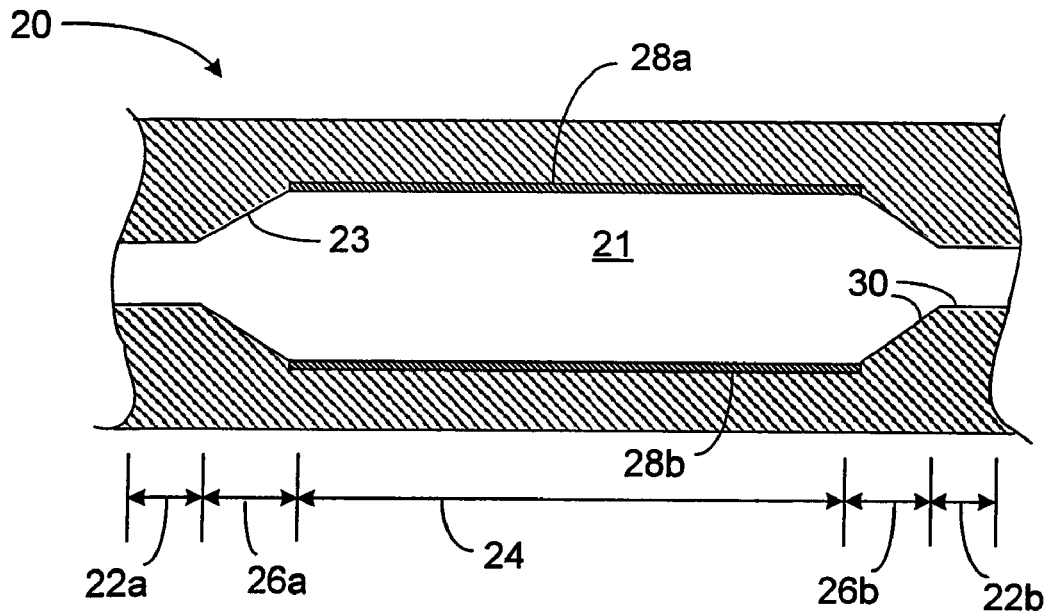
FIG. 12 is a cross-sectional view of an embodiment of a mold.
Figure 13:
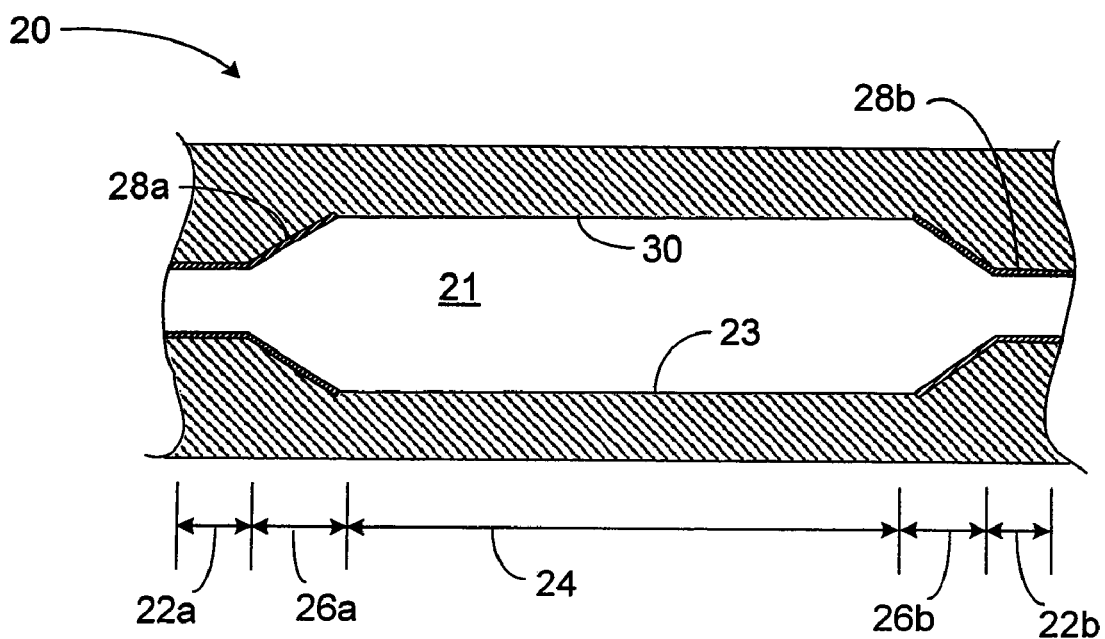
FIG. 13 is a cross-sectional view of an embodiment of a mold.
Figure 14:
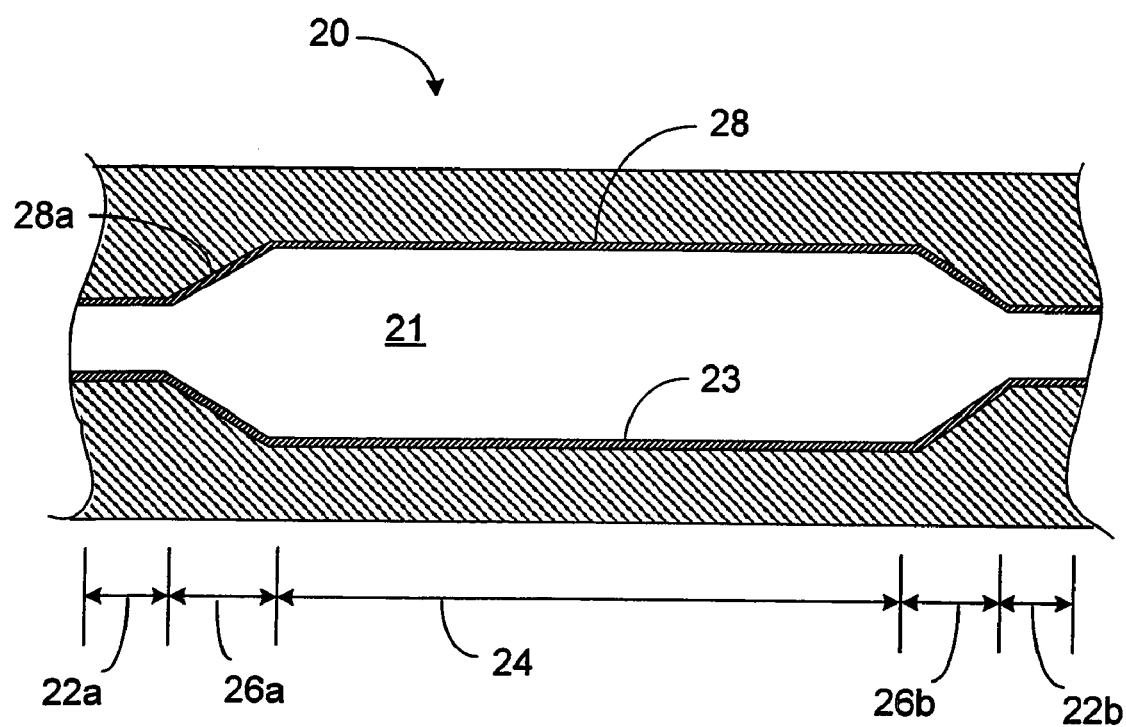
FIG. 14 is a cross-sectional view of an embodiment of a mold.

FIGS. 12-14 illustrate some alternative embodiments with mold portions having a relatively low coefficient of friction (e.g., in the form of a coating, an insert or a composite material) located at various positions along exposed surface 27 of mold 20. In FIG. 12, portions 28a and 28b are located only within body region 24 of cavity 21. FIG. 13 illustrates portions 28a and 28b (e.g., in the form of a coating, an insert or a composite material) located only within waist regions 22a, 22b and cone regions 26a, 26b. In FIG. 14, portions 28a and 28b (e.g., in the form of a coating, an insert or a composite material) located within each of body 24, waist 22a, 22b and cone 26a, 26b regions. In some cases, portions 28, 28a and 28b having the lower coefficient of friction can be located only within waist portions 22a, 22b.

In some embodiments, the mold may have only one relatively low coefficient of friction portion. In certain embodiments, the mold may have three or more (e.g., four, five, six, seven, eight, nine, 10) portions with a relatively low coefficient of friction. The relatively low coefficient of friction portions may be contiguous or noncontiguous.

In certain embodiments in which the mold includes multiple portions with a low coefficient of friction, one or more low coefficient of friction portions may be formed by different techniques. As an example, one or more low coefficient of friction portions may be formed by liquid deposition and one or more low coefficient of friction portions may be formed of a composite material. As another example, one or more low coefficient of friction portions may be formed by liquid deposition and one or more low coefficient of friction portions may be formed of an insert. As an additional example, one or more low coefficient of friction portions may be formed of an insert and one or more low coefficient of friction portions may be formed of a composite material.

In some embodiments in which the mold includes multiple portions with a low coefficient of friction, one or more of the low coefficient of friction portions may have a different coefficient of friction from one or more of the other low coefficient of friction portions.

In certain embodiments, one or more low coefficient of friction portions of the mold may not be formed in a recess in body of the mold.

In some embodiments, molds can be applied to other balloon configurations (e.g., step or non-regular balloons).

In certain embodiments, a coronary balloon can have a diameter of from about 1.5 millimeters to about six millimeters. In some embodiments, a peripheral balloon can have a diameter of from about three millimeters to about 12 millimeters. In certain embodiments, an endoscopy and/or urology balloon can have a diameter of from about four millimeters to about 40 millimeters. In some embodiments, a neurology balloon can have a diameter of from about 1.5 millimeters to about five millimeters.

The following examples are intended as illustrative and not limiting.

EXAMPLE I

A cast aluminum, two-piece clamshell mold for forming a medical balloon having an eight-millimeter expanded diameter was formed as described below. The mold included an exposed inner surface forming a mold cavity with a 0.043 inch (0.108 cm) inner diameter within the proximal waist region, a 0.284 inch (0.721 cm) inner diameter within the body region, a 0.035 inch (0.09 cm) inner diameter within the distal waist region and a 25 degree taper angle within the cone regions. The exposed surface within the cone, body and waist regions of the mold was formed of a $5 \times 10^{-4}$ inch thick hardcoat anodized coating with Teflon®, providing a coefficient of friction within the coated regions of about 0.073. The anodized coating was applied by treating the aluminum electrolytically to produce a uniform anodic coating on the metal surface within the cone and waist regions. After forming the anodic coating, Teflon® was applied to the unsealed surface of the anodic coating and then cured at 177° C. for one hour.

An eight-millimeter expanded diameter medical balloon was formed using the mold described above in an infrared, dual-end tension molding process as follows. A 14-inch long tube of 7233 PEBAX® having an outer diameter of 0.0862 inch and an inner diameter of 0.0522 inch was extruded. About ⅓ of the extruded tube, corresponding to a region of the extruded tube where the body of the medical balloon was to be formed, was frozen using a −62° F. aerosol freeze spray. While frozen, the extruded tube was transferred to a pre-stretching station where the tube was stretched axially in a pre-forming process at room temperature under about 24.5 lbs of tension applied to both ends of the tube to form a parison. Within the frozen region, the parison remained relatively unstretched while outside the body region the parison was drawn to a draw ratio of about 3.5. The parison was then transferred to the mold to form the balloon. The tube was placed in dual end tension with both ends of the tube pre-loaded at about 30 lbs of tension and the tube was pressurized with air at a minimum internal air pressure of about 400 psi. The parison was heated from room temperature to about 95° C. over a period of about 60 seconds by heating the mold using a Model 5305 single stage infrared light, available from Research Inc., at Eden Prairie, Minn. In about 30 seconds, the glass transition temperature of the balloon material (about 65° C.) was reached and the parison expanded relatively rapidly (about 0.2 second) forming the balloon shape. The balloon material continued to be heated to about 95° C. over an additional period of about 30 seconds (for a total of 60 seconds) and was maintained at about 95° C. for about 30 seconds for a total cycle time of about 1.5 minutes. Then, the infrared light was turned off and the mold was force quenched to about 50° C. by spraying the mold with water at room temperature and the upper half of the mold was lifted to remove the formed balloon.

The medical balloon formed using the above-described mold and process had a distal cone wall thickness of $1.515 \times 10^{-3}$ inch and a proximal cone wall thickness of $1.67 \times 10^{-3}$ inch, both measured by folding the balloon and measuring a 2× wall thickness using a drop gauge.

To measure compressed profile diameters of the balloon, the balloon was laser bonded to a catheter shaft having an outer diameter of 0.047 inch and the balloon was wrapped about the catheter shaft in a five-point star configuration using crimping blades to form a compressed profile. The wrapped balloon was measured using a drop gauge to determine the maximum wrapped profile diameter of the wrapped balloon. The maximum wrapped profile diameter was 0.059 inch, or about 1.26 times the outer diameter of the shaft, and was located in the cone region of the balloon.

EXAMPLE II

A cast aluminum, two-piece clamshell mold for forming a medical balloon having a 14-millimeter expanded diameter was formed as described below. The mold included an exposed inner surface forming a mold cavity with a 0.061 inch (0.156 cm) inner diameter within the proximal waist region, a 0.532 inch (1.351 cm) inner diameter within the body region, a 0.045 inch (0.114 cm) inner diameter within the distal waist region and a 25 degree taper angle within the cone regions. The exposed surface within the cone, body and waist regions of the mold was formed of a $5 \times 10^{-4}$ inch thick hardcoat anodized coating with Teflon®, providing a coefficient of friction within the coated regions of about 0.073. The anodized coating was applied by treating the aluminum electrolytically to produce a uniform anodic coating on the metal surface within the cone and waist regions. After forming the anodic coating, Teflon® was applied to the unsealed surface of the anodic coating and then cured at 177° C. for one hour.

A 14-millimeter expanded diameter medical balloon was formed using the mold described above in an infrared, dual-end tension molding process as follows. A 14-inch long tube of 7233 PEBAX® having an outer diameter of 0.1362 inch and an inner diameter of 0.0882 inch was extruded. About ⅓ of the extruded tube, corresponding to a region of the extruded tube where the body of the medical balloon was to be formed, was frozen using a −62° F. aerosol freeze spray. The extruded tube was then transferred to a prestretching station where the tube was stretched axially, with the body-forming region still frozen, in a pre-forming process at room temperature under about 44.75 lbs of tension applied to both ends of the tube to form a parison. Within the frozen region, the parison remained relatively unstretched while outside the body region the parison was drawn to a draw ratio of about 3.5. The parison was then transferred to the mold to form the balloon. The tube was placed in dual end tension with both ends of the tube preloaded at about 46 lbs of tension and the tube was pressurized with air at a minimum internal air pressure of about 400 psi. The parison was heated from room temperature to about 95° C. over a period of about 60 seconds by heating the mold using a Model 5305 single stage infrared light, available from Research Inc., at Eden Prairie, Minn. In about 30 seconds, the glass transition temperature of the balloon material (about 65° C.) was reached and the parison expanded relatively rapidly (about 0.2 second) forming the balloon shape. The balloon material continued to be heated to about 95° C. over an additional period of about 30 seconds (for a total of 60 seconds) and was maintained at about 95° C. for about 30 seconds for a total cycle time of about 1.5 minutes. Then, the infrared light was turned off and the mold was force quenched to about 50° C. by spraying the mold with water at room temperature and the upper half of the mold was lifted to remove the formed balloon.

The medical balloon formed using the above-described mold and process had a wall thickness of about $2.23 \times 10^{-3}$ inch in both the proximal and distal cone regions, both measured by folding the balloon and measuring a 2× wall thickness using a drop gauge.

To measure compressed profile diameters of the balloon, the balloon was laser bonded to a catheter shaft having an outer diameter of 0.078 inch and the balloon was wrapped about the catheter shaft in a five-point star configuration using crimping blades to form a compressed profile. The wrapped balloon was measured using a drop gauge to determine the maximum wrapped profile diameter of the wrapped balloon. The maximum wrapped profile diameter was 0.082 inch, or about 1.05 times the outer diameter of the shaft, and was located in the cone region of the balloon.

EXAMPLE III

A cast aluminum, two-piece clamshell mold for forming a medical balloon having an eight-millimeter expanded diameter was formed with identical dimensions as those of Example I, with the exposed surface within only the cone and waist regions of the mold being formed of a $5 \times 10^{-4}$ inch thick hardcoat anodized coating with Teflon®, providing an average coefficient of friction within the coated regions of about 0.073. The exposed surface within the body region was formed of the aluminum mold material. As above, the anodized coating was applied by treating the aluminum electrolytically to produce a uniform anodic coating on the metal surface within the cone and waist regions. After forming the anodic coating, Teflon® was applied to the unsealed surface of the anodic coating and then cured at 177° C. for one hour.

EXAMPLE IV

A cast aluminum, two-piece clamshell mold for forming a medical balloon having a 14-millimeter expanded diameter was formed with identical dimensions as those of Example II, with the exposed surface within only the cone and waist regions of the mold being formed of a $5 \times 10^{-4}$ inch thick hardcoat anodized coating with Teflon®, providing an average coefficient of friction within the coated regions of about 0.073. The exposed surface within the body region was formed of the aluminum mold material. As above, the anodized coating was applied by treating the aluminum electrolytically to produce a uniform anodic coating on the metal surface within the cone and waist regions. After forming the anodic coating, Teflon® was applied to the unsealed surface of the anodic coating and then cured at 177° C. for one hour.

EXAMPLE V

A cast aluminum, two-piece clamshell mold for forming a medical balloon having an eight-millimeter expanded diameter was formed with identical dimensions as those of Examples I and III, with the exposed surface within the cone, body and waist regions of the mold being formed of a $2 \times 10^{-6}$ inch thick Dicronite® modified tungsten disulfide coating, available from and applied at Dicronite Dry Lube of Minnesota providing an average coefficient of friction within the coated regions of about 0.28.

EXAMPLE VI

A cast aluminum, two-piece clamshell mold for forming a medical balloon having a 14-millimeter expanded diameter was formed with identical dimensions as those of Examples II and IV, with the exposed surface within the cone, body and waist regions of the mold being formed of a $2 \times 10^{-6}$ inch thick Dicronite® modified tungsten disulfide coating, available from and applied at Dicronite Dry Lube of Minnesota providing an average coefficient of friction within the coated regions of about 0.28.

EXAMPLE VII

A cast aluminum, two-piece clamshell mold for forming a medical balloon having an eight-millimeter expanded diameter was formed with identical dimensions as those of Examples I, III and V with the exposed surface within only the cone and waist regions of the mold being formed of a $2 \times 10^{-6}$ inch thick Dicronite® modified tungsten disulfide coating, available from and applied at Dicronite Dry Lube of Minnesota providing an average coefficient of friction within the coated regions of about 0.28. The exposed surface within the body region was formed of the aluminum mold material.

EXAMPLE VIII

A cast aluminum, two-piece clamshell mold for forming a medical balloon having a 14-millimeter expanded diameter was formed with identical dimensions as those of Examples II, IV and VI with the exposed surface within only the cone and waist regions of the mold being formed of a $2 \times 10^{-6}$ inch thick Dicronite® modified tungsten disulfide coating, available from and applied at Dicronite Dry Lube of Minnesota providing an average coefficient of friction within the coated regions of about 0.28. The exposed surface within the body region was formed of the aluminum mold material.

Other embodiments are within the claims.

What is claimed is:

1. A mold having an exposed surface defining a mold cavity, the mold cavity having a body region, a waist region and a cone region connecting the body and waist regions, wherein a first portion of the exposed surface has a first coefficient of friction, and a second portion of the exposed surface has a second coefficient of friction, the first coefficient of friction being different from the second coefficient of friction,
wherein the first portion of the exposed surface comprises a composite material including a mold material and a mold material additive.

2. The mold of claim 1, wherein the first coefficient of friction is at most about 0.8.

3. The mold of claim 1, wherein the first coefficient of friction is at most about 0.4.

4. The mold of claim 1, wherein a ratio of the first coefficient of friction to the second coefficient of friction is less than about 0.5.

5. The mold of claim 1, wherein the first portion of the exposed surface is contained within only the waist region.

6. The mold of claim 1, wherein the first portion of the exposed surface is contained within only two regions selected from the group consisting of the body region, the waist region and the cone region.

7. The mold of claim 1, wherein the first portion of the exposed surface is contained within only the waist and cone regions.

8. The mold of claim 1, wherein the mold comprises a mold body and a coating supported by the mold body so that the coating forms the first portion of the exposed surface of the mold.

9. The mold of claim 8, wherein the coating comprises a material selected from the group consisting of fluorinated polymers, carbon-based materials, silicones, polyethylenes, tungsten disulfide, polyetheretherketones and combinations thereof.

10. The mold of claim 1, wherein the mold comprises a mold body and an insert supported by the mold body so that the insert forms the first portion of the exposed surface of the mold.

11. The mold of claim 1, wherein the first portion of the exposed surface comprises a material selected from the group consisting of fluorinated polymers, carbon-based materials, silicones, polyethylenes, tungsten disulfide, polyetheretherketones and combinations thereof.

12. The mold of claim 1, wherein the waist region of the mold cavity has an inner diameter of greater than about 0.75 mm.

13. The mold of claim 1, wherein the body region of the mold cavity has an inner diameter of at most about 40 mm.

14. The mold of claim 1, wherein the cone region of the mold cavity has a taper of at least about 10 degrees.

15. The mold of claim 1, wherein the mold cavity has a maximum inner diameter of at most about 40 mm and the mold cavity has a minimum inner diameter within the cavity of at most about 1 mm.

16. The mold of claim 1, wherein the mold comprises a mold body including first and second pieces, the first and second pieces being configured to releasably fit together to define the mold cavity.

* * * * *